(12) United States Patent
Naito et al.

(10) Patent No.: US 11,534,347 B2
(45) Date of Patent: Dec. 27, 2022

(54) CIRCUIT, DETECTOR, WIRELESS COMMUNICATION DEVICE, MOISTURE SENSING SYSTEM, DIAPER, NOTIFICATION SYSTEM, AND CIRCUIT MANUFACTURING METHOD

(71) Applicant: TORAY INDUSTRIES, INC., Tokyo (JP)

(72) Inventors: Kojiro Naito, Shiga (JP); Shota Kawai, Shiga (JP); Junji Wakita, Shiga (JP); Kenta Noguchi, Shiga (JP); Seiichiro Murase, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 310 days.

(21) Appl. No.: 16/767,261

(22) PCT Filed: Nov. 15, 2018

(86) PCT No.: PCT/JP2018/042232
§ 371 (c)(1),
(2) Date: May 27, 2020

(87) PCT Pub. No.: WO2019/107165
PCT Pub. Date: Jun. 6, 2019

(65) Prior Publication Data
US 2020/0405546 A1  Dec. 31, 2020

(30) Foreign Application Priority Data

Nov. 30, 2017 (JP) .............................. JP2017-230735
Feb. 27, 2018 (JP) .............................. JP2018-033755

(51) Int. Cl.
*A61F 13/42* (2006.01)
*G01N 27/04* (2006.01)
*A61F 5/44* (2006.01)

(52) U.S. Cl.
CPC ............. *A61F 13/42* (2013.01); *G01N 27/04* (2013.01); *A61F 2005/4402* (2013.01); *A61F 2013/424* (2013.01); *A61F 2013/428* (2013.01)

(58) Field of Classification Search
CPC ................ A61F 13/42; A16F 2013/424; A16F 2013/428
See application file for complete search history.

(56) References Cited

U.S. PATENT DOCUMENTS

| 4,325,223 A | * | 4/1982 | Cantley | .................. F25B 49/02 |
| | | | | 702/182 |
| 5,189,812 A | * | 3/1993 | Ediger | .................. F26B 17/122 |
| | | | | 34/174 |

(Continued)

FOREIGN PATENT DOCUMENTS

| CN | 1380547 A | 11/2002 |
| CN | 102043000 A | 5/2011 |

(Continued)

OTHER PUBLICATIONS

Taiwanese Office Action and Search Report for Taiwanese Application No. 107141703, dated Oct. 1, 2021, with an English translation.

(Continued)

*Primary Examiner* — Hoi C Lau
(74) *Attorney, Agent, or Firm* — Birch, Stewart, Kolasch & Birch, LLP

(57) ABSTRACT

The present invention provides a circuit including a plurality of component parts formed on a substrate and having common functions, wherein the plurality of component parts each includes a detection part which shows responsiveness to moisture; wherein the responsiveness to moisture varies between the plurality of component parts; and wherein the presence or absence of a response to moisture detected by (Continued)

each detection part corresponds to a binary digital signal, and whereby the circuit outputs a sequence of binary digital signals.

20 Claims, 11 Drawing Sheets

(56) References Cited

U.S. PATENT DOCUMENTS

| | | | |
|---|---|---|---|
| 5,424,881 A * | 6/1995 | Behrens | H03M 13/31 |
| 6,832,507 B1 | 12/2004 | Van de Berg et al. | |
| 11,399,988 B2 * | 8/2022 | Kawai | H01L 51/00 |
| 2004/0038484 A1 | 2/2004 | Tamai | |
| 2004/0230172 A1 | 11/2004 | Shapira | |
| 2011/0088466 A1 | 4/2011 | Frerichs | |
| 2013/0018231 A1 | 1/2013 | Hong et al. | |
| 2014/0006660 A1 * | 1/2014 | Frei | H04L 12/281 710/104 |
| 2014/0182362 A1 | 7/2014 | Potyrailo et al. | |
| 2015/0320609 A1 | 11/2015 | Thoen | |
| 2016/0003770 A1 | 1/2016 | Klootwijk et al. | |
| 2016/0020599 A1 | 1/2016 | Harper et al. | |
| 2016/0374868 A1 | 12/2016 | Ettrup Hansen | |
| 2017/0076676 A1 | 3/2017 | Hadwen | |
| 2018/0021183 A1 | 1/2018 | Teng | |
| 2020/0261278 A1 * | 8/2020 | Kawai | H01L 51/00 |
| 2020/0405546 A1 * | 12/2020 | Naito | A61F 5/44 |

FOREIGN PATENT DOCUMENTS

| | | |
|---|---|---|
| CN | 102871801 A | 1/2013 |
| CN | 103528603 A | 1/2014 |
| CN | 105686905 A | 6/2016 |
| CN | 106463040 A | 2/2017 |
| JP | 6-75448 U | 10/1994 |
| JP | 9-33468 A | 2/1997 |
| JP | 2004-49470 A | 2/2004 |
| JP | 2006-504976 A | 2/2006 |
| JP | 2006-349418 A | 12/2006 |
| JP | 2007-296024 A | 11/2007 |
| JP | 2011-235079 A | 11/2011 |
| JP | 2013-195364 A | 9/2013 |
| JP | 5383891 B1 | 1/2014 |
| JP | 2014-29315 A | 2/2014 |
| JP | 2015-531491 A | 11/2015 |
| JP | 2016-505850 A | 2/2016 |
| JP | 2016-524161 A | 8/2016 |
| JP | 2017-507325 A | 3/2017 |
| TW | I424157 B | 1/2014 |
| TW | I630959 B | 8/2018 |
| WO | WO 97/42613 A2 | 11/1997 |
| WO | WO 2015/137999 A1 | 9/2015 |
| WO | WO 2015/140394 A1 | 9/2015 |
| WO | WO 2017/047086 A1 | 3/2017 |

OTHER PUBLICATIONS

International Search Report, issued in PCT/JP2018/042232, PCT/ISA/210, dated Feb. 5, 2019.
Written Opinion of the International Searching Authority, issued in PCT/JP2018/042232, PCT/ISA/237, dated Feb. 5, 2019.
Chinese Office Action and Search Report for Chinese Application No. 201880072236.2, dated Sep. 29. 2022, with an English translation of the Chinese Office Action.

* cited by examiner

CIRCUIT, DETECTOR, WIRELESS COMMUNICATION DEVICE, MOISTURE SENSING SYSTEM, DIAPER, NOTIFICATION SYSTEM, AND CIRCUIT MANUFACTURING METHOD

TECHNICAL FIELD

The present invention relates to a circuit, a detector, a wireless communication device, a moisture detection system, a diaper, a notification system and a method of producing the circuit.

BACKGROUND ART

Techniques for detecting moisture are important in various fields. The field in which such an importance is particularly increasing may be, for example, the field of diapers to be worn by care receivers, such as senior citizens who require nursing. In societies with growing number of senior citizens, it is possible to reduce the burdens on both care givers and care receivers, if diapers are capable of detecting moisture generated due to urination and the like of the care receivers. Therefore, the application of moisture detection techniques in the field of diapers is drawing attention, in recent years.

From the viewpoint of practical use, it is desirable that diapers be capable of detecting not only the presence of moisture, but also the amount of moisture present, and that the measured results can be delivered to measurers by wireless communications, not by wired communications.

There are various kinds of techniques for measuring moisture. Examples include a technique in which the amount of moisture is detected by the degree of conduction between electrodes when the electrodes are connected by moisture (see, for example, Patent Literature 1), a technique in which an AC voltage is applied between electrodes, and the amount of moisture is detected by changes in electrostatic capacity (see, for example, Patent Literature 2), and the like.

CITATION LIST

Patent Literature

Patent Literature 1: JP 2007-296024 A
Patent Literature 2: JP 2016-524161 A

SUMMARY OF INVENTION

Technical Problem

However, in the technique disclosed in Patent Literature 1 or 2, changes which occur in a detector during the process of detection were obtained as analog data. Therefore, a complex circuit for converting the analog data of the amount of changes to digital data is required in the detector, in order to transmit the detection results in a wireless communication. An increase in the complexity of the circuit leads to an increase in the size of the detector and an increase in the production cost of a measuring apparatus, which are problematic. Accordingly, a technique has been demanded which is capable of accurately detecting not only the presence or absence of moisture, but also the amount of moisture in contact, with a simple and economically efficient configuration.

The present invention has been made in view of the above described problems, and an object of the invention is to provide: a circuit capable of accurately detecting not only the presence or absence of moisture, but also the amount of moisture in contact, with a simple and economically efficient configuration; a detector, a wireless communication device, a moisture detection system, a diaper and a notification system including the circuit; as well as a method of producing the circuit.

Means for Solving the Problems

In order to solve the above mentioned problems and to achieve the object of the invention, the circuit according to the present invention includes a plurality of component parts formed on a substrate and having common functions, wherein the plurality of component parts each includes a detection part which shows responsiveness to moisture;
wherein the responsiveness to moisture varies between the plurality of component parts; and
wherein the presence or absence of a response to moisture detected by each detection part corresponds to a binary digital signal, and whereby the circuit outputs a sequence of binary digital signals.

The detector according to the present invention includes the above described circuit.

The wireless communication device according to the present invention includes:
the above described circuit; and
an antenna which is connected to the circuit and which transmits and receives signals to and from a transceiver in a non-contact manner.

The moisture detection system according to the present invention includes:
the above described wireless communication device; and
a transceiver which is capable of communicating with the wireless communication device in a non-contact manner, and which detects the presence or absence of contact between the wireless communication device with moisture and/or the amount of moisture in contact, based on the signal returned in response to the signal transmitted to the wireless communication device.

The diaper according to the present invention includes:
a water absorbent material which absorbs and retains moisture; and
a waterproof material having a waterproof function and covering the water absorbent material;
wherein the diaper is capable of being attached to a human body and absorbing moisture released from the human body; and
wherein the diaper includes the above described wireless communication device.

The notification system according to the present invention includes:
the above described diaper; and
a device which notifies that the diaper is in contact with moisture.

The method of producing the above described circuit, according to the present invention, includes the step of forming the semiconductor layer in the transistor by application method.

Effect of the Invention

According to the present invention, it is possible to accurately detect not only the presence or absence of moisture, but also the amount of moisture in contact, with a simple and economically efficient configuration.

MODE FOR CARRYING OUT THE INVENTION

The embodiments for carrying out the present invention (hereinafter, each referred to as "embodiment") will now be described with reference to the accompanying drawings. It is noted that the drawings are merely schematic representations.

Embodiment 1

Figure 1:
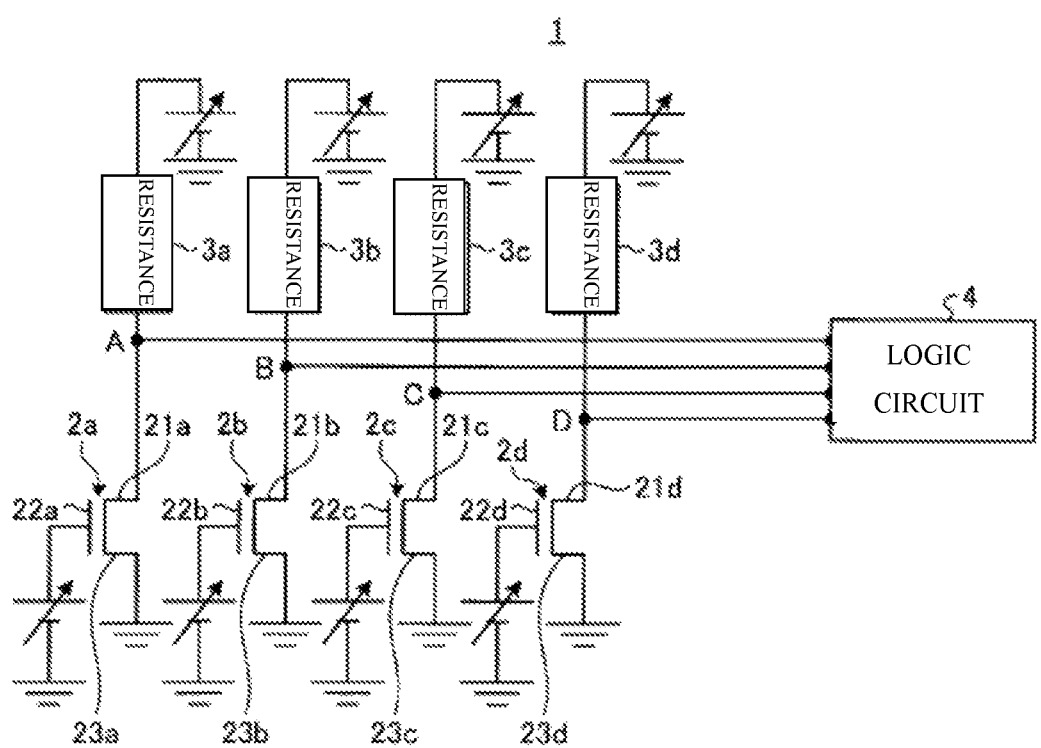
FIG. 1 is a diagram showing the structure of the circuit according to Embodiment 1 of the present invention.

FIG. 1 is a diagram showing the structure of the circuit according to Embodiment 1 of the present invention. A circuit 1 shown in FIG. 1 includes: transistors $2a$ to $2d$, which are four component parts arranged in parallel; four resistances $3a$ to $3d$, and a logic circuit 4. The transistor $2a$ includes a source electrode (a first electrode) $21a$, a gate electrode $22a$ (a third electrode) and a drain electrode $23a$ (a second electrode). The source electrode $21a$ is connected to the resistance $3a$ through a wiring, and is also electrically connected to the logic circuit 4 through another wiring branching from a connecting point A in the wiring. The transistors $2b$ to $2d$ have the same configuration as the transistor $2a$, and are connected to the resistances $3b$ to $3d$, respectively, and to the logic circuit 4. In the circuit 1, the transistors $2a$ to $2d$ each includes a detection part thereon. The number of transistors shown in FIG. 1 is merely one example, and the number is, of course, not limited to four. Further, as a modified example of FIG. 1, each of the resistances $3a$ to $3d$ may be replaced with a transistor. Unlike a resistance, a transistor is characterized in that the relationship between the applied voltage and the current is not proportional. Whether to select resistances or transistors for the configuration of the circuit may be determined taking into consideration the balance with the properties of other elements constituting the circuit.

The wirings connecting between the transistors $2a$ to $2d$ and the resistances $3a$ to $3d$ are electrically connected to the logic circuit 4 at the connecting points A to D. The currents flowing from the connecting points A to D or the voltages at the connecting points A to D are each recognized by the logic circuit 4 as "0" or "1", which is a binary digital signal, and then converted into a digital signal sequence. Specifically, values of the signals transmitted from the connecting points A to D are signal values (parallel) that are in parallel with each other, which are then converted to a signal sequence (serial). This conversion is carried out by a flip-flop circuit and a clock signal circuit included in the logic circuit 4.

Figure 2A:
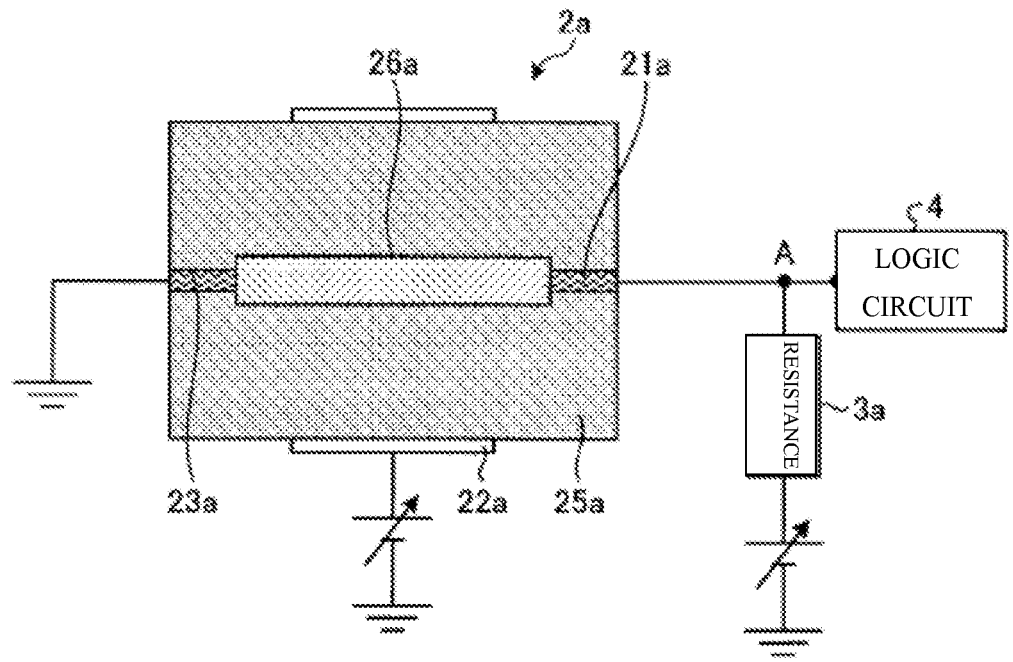
FIG. 2A is a plan view showing the configuration of a transistor included in the circuit according to Embodiment 1 of the present invention.
Figure 2B:
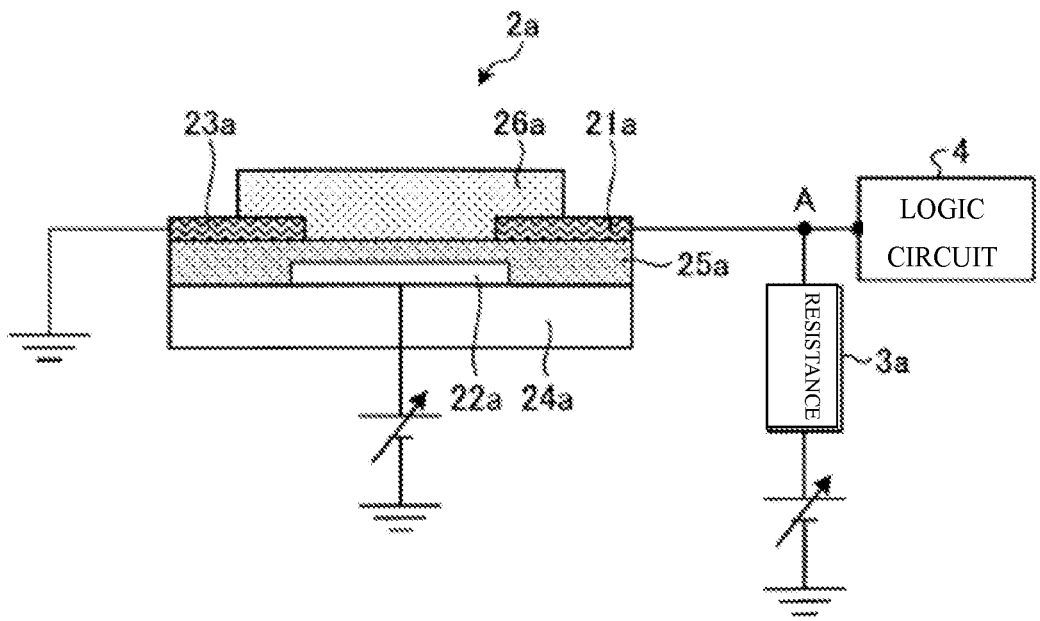
FIG. 2B is a sectional view showing the configuration of the transistor included in the circuit according to Embodiment 1 of the present invention.

The configuration of the transistor $2a$ will now be described. The configurations of the transistors $2b$ to $2d$ are the same as that of the transistor $2a$. FIG. 2A is a plan view showing the configuration of the transistor $2a$. FIG. 2B is a sectional view showing the configuration of the transistor $2a$. The transistor $2a$ includes: the source electrode $21a$, the gate electrode $22a$, the drain electrode $23a$, a substrate $24a$, an insulating layer $25a$ and a semiconductor layer $26a$. The gate electrode $22a$ is electrically insulated from the source electrode $21a$ and the drain electrode $23a$ by the insulating layer $25a$. Further, the semiconductor layer $26a$ is formed between the source electrode $21a$ and the drain electrode $23a$. The transistor $2a$ is a bottom-contact/bottom-gate type transistor. In cases where the detection part is provided on the transistor $2a$, the semiconductor to be used in the transistor $2a$ is not particularly limited, and any semiconductor such as an element semiconductor, a compound semiconductor, an organic semiconductor or a nanocarbon material can be used. However, an organic semiconductor or a nanocarbon material is preferred, since the properties thereof easily change when coming into contact with moisture.

Changes in the properties of the semiconductor layer in the transistor cause changes in the current value or the voltage value. When the semiconductor layer in each transistor comes into contact with moisture to cause changes in the properties thereof, it causes the signal value to be output from each transistor to change from "0" to "1", or from "1" to "0".

The "moisture" as used herein refers to a liquid containing 50% by mole or more of $H_2O$. It is noted, however, that a liquid in which hydrogen is replaced with deuterium or tritium is also considered as H₂O. Further, the moisture does not necessarily be present only in a liquid state, but may be present in a state contained in a water-absorbent polymer. Even in such a case, water on the surface of the polymer acts on a detector 101 to be described later, to provide the same effect. This is the reason why the detector 101 is suitably used in a diaper 204 to be described later.

Examples of the organic semiconductor include polythiophenes, polypyrroles, poly(p-phenylene vinylene)s, polyanilines, polyacetylenes, polydiacetylenes, polycarbazoles, polyfurans, polyheteroaryls, condensed polycyclic low-molecular-weight compound semiconductors, low-molecular-weight compound semiconductors containing a heteroaromatic ring. Examples of the polythiophenes include poly-3-hexylthiophene and polybenzothiophene. Examples of the polyfurans include polyfuran and polybenzofuran. Examples of the polyheteroaryls include those containing a nitrogen-containing aromatic ring as a structural unit, such as pyridine, quinoline, phenanthroline, oxazole and oxadiazole. Examples of the condensed polycyclic low-molecular-weight compound semiconductors include anthracene, pyrene, naphthacene, pentacene, hexacene and rubrene. Examples of the low-molecular-weight compound semiconductors containing a heteroaromatic ring include furan, thiophene, benzothiophene, dibenzofuran, pyridine, quinoline, phenanthroline, oxazole and oxadiazole.

Examples of the nanocarbon material include fullerene, carbon nanotubes, graphene and carbon nanohorns.

Among these materials, an organic semiconductor or a carbon nanotube is more preferred, since it enables the formation of the semiconductor layer on a film by an application method, and thus allows for an easier production as compared to commonly used materials such as silicon (Si) and a reduction in cost. From the viewpoint of enabling the formation of the semiconductor layer at a low temperature of 200° C. or lower, and having high semiconductor properties, a carbon nanotube is still more preferred. Among carbon nanotubes, a single☐walled carbon nanotube is particularly preferred, because of its excellent semiconductor properties.

Among carbon nanotubes, particularly preferred is a carbon nanotube composite having a conjugated polymer attached to at least a part of the surface thereof. This is because the use of such a carbon nanotube composite enables to uniformly disperse the carbon nanotube in a solution, without compromising high electrical properties of the carbon nanotube. By using a solution in which a carbon nanotube is uniformly dispersed, it is possible to form a film in which the carbon nanotube is uniformly dispersed, by an application method such as an ink jet method. Among conjugated polymers, a polythiophene-based polymer, a polybenzothiadiazole-based polymer, a poly(alkylfluorene)-based polymer, or the like is preferred, because of its high ability to disperse a carbon nanotube.

The substrate may be made of any material, as long as at least the surface of the substrate on which the electrode system is provided has insulation properties. Examples of the material which can be suitably used include: inorganic materials such as silicon wafers, glass, sapphire and alumina sintered bodies; and organic materials such as polyimides, polyvinyl alcohol, polyvinyl chloride, polyethylene terephthalate, polvinylidene fluoride, polysiloxanes, polyvinyl phenol (PVP), polyesters, polycarbonates, polysulfone, polyethersulfone, polyethylene, polyphenylene sulfide and polyparaxylene. Further, the substrate may be, for example, a substrate obtained by laminating a plurality of materials, such as one obtained by forming a PVP film on a silicon wafer, or one obtained by forming a polysiloxane film on a polyethylene terephthalate substrate.

The material to be used for forming the insulating layer is not particularly limited, as long as the material has insulation properties sufficient for the resulting insulating layer to function properly. Examples of the material which can be used include polysiloxanes, polyamides, polyamideimides, polyimides, polybenzimidazole, polyvinyl alcohol, polyvinyl phenol, polyacetal, polycarbonates, polyarylates, polyphenylene sulfide, polyethersulfone, polyether ketone, polyphthalamide, polyether nitrile, polymethyl methacrylate, polymethacrylamide, polyvinylidene fluoride, polytetrafluoroethylene, polystyrene, parylene, polyesters, aromatic polyethers, novolac resins, phenol resins, acrylic resins, olefin resins, alicyclic olefin resins, vinyl chloride resins, epoxy resins, melamine resins and urea resins. Further, it is also possible to use a material obtained by copolymerizing or mixing any of these polymers with another polymer(s). Among these, a polysiloxane is preferably used, from the viewpoint of improving the on-current of the transistor, and reducing the leak current thereof.

The insulating layer is composed of a single layer or a plurality of layers. In cases where the insulating layer is composed of a plurality of layers, the insulating layer may be formed by laminating a plurality of the insulating layers, or by laminating the insulating layer with a known gate insulating layer(s). Further, it is also possible to provide an orientation layer between the insulating layer and the semiconductor layer. A known material(s) such as a silane compound, a titanium compound, an organic acid, a heteroorganic acid and/or the like can be used for forming the orientation layer, and an organic silane compound is particularly preferred.

Figure 3:
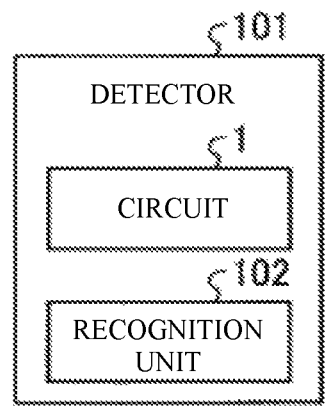
FIG. 3 is a diagram showing the configuration of the detector according to Embodiment 1 of the present invention.

The circuit 1 having the above described configuration constitute a part of the detector 101 shown in FIG. 3. The detector 101 has the function of detecting the presence or absence of contact with moisture and/or the amount of moisture in contact. The detector 101 includes: the circuit 1; and a recognition unit 102 which recognizes a sequence of binary digital signals output by the circuit 1. The recognition unit 102 may be a circuit for recognizing a sequence of digital signals, or alternatively, a light emitting element, a sound generating element or the like.

Figure 4:
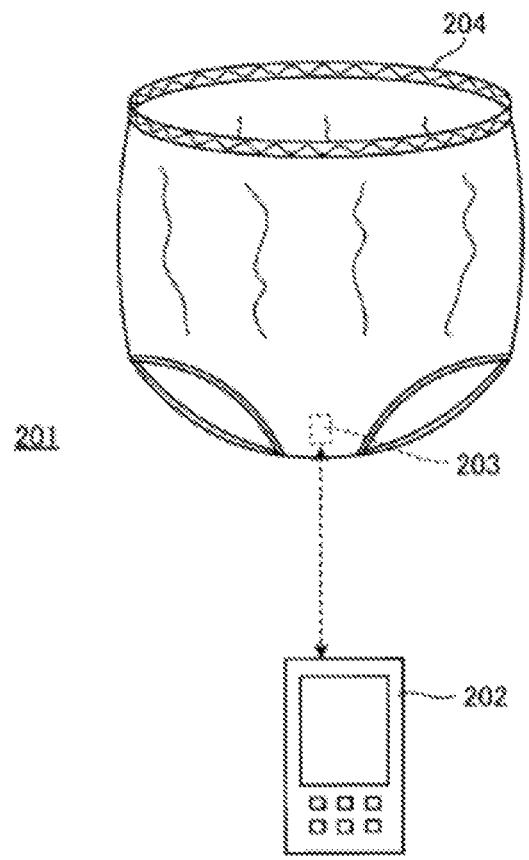
FIG. 4 is a diagram showing the configuration of the moisture detection system according to Embodiment 1 of the present invention.

FIG. 4 is a diagram showing the configuration of the moisture detection system including the circuit 1. A moisture detection system 201 shown in FIG. 4 includes: a transceiver 202 which wirelessly transmits and receives signals in a predetermined frequency band; and the diaper 204 which includes a wireless communication device 203 capable of non-contact communication (wireless communication) with the transceiver 202, and which is capable of being attached to a human body and absorbing moisture at the time of urination. The moisture detection system 201 is a system for detecting the generation of moisture due to urination and the like of a person wearing the diaper 204, and therefore, it can be said that the moisture detection system 201 is a wetness detection system using the diaper 204. Further, the wireless communication device 203 can be considered as one example of the above described detector 101.

The transceiver 202 includes: an antenna which transmits and receives signals in a predetermined frequency band; a CPU (Central Processing Unit) for controlling operations; and a memory for storing various types of information. The transceiver 202 transmits a signal (carrier wave) in a predetermined frequency band to the wireless communication device 203, and receives a return signal in response to the transmitted signal. The return signal includes information specific to the wireless communication device 203. The transceiver 202 distinguishes the wireless communication device 203 based on the signal received from the wireless communication device 203, and at the same time, detects whether the wireless communication device 203 is in a state in contact with moisture or not. The signal to be transmitted by the transceiver 202 is, for example, a signal having a frequency in the UHF band (from 860 to 960 MHz), or in the L band (a frequency of from 1 to 2 GHz) or the S band (a frequency 2 to 4 GHz) of the microwave spectrum. The transceiver 202 as described above may be configured, for example, as a dedicated terminal such as a reader/writer, or may be configured using a mobile terminal such as a smart phone. Further, the communication between the transceiver and the wireless communication device may be achieved by NFC Communication (Near Field Communication) at a frequency of 13.56 MHz. In cases where the moisture detector according to the present invention is used in the wetness detection in a diaper, for example, the wireless communication device can be installed to a bed sheet or the like, so as to detect the presence of moisture.

Figure 5:
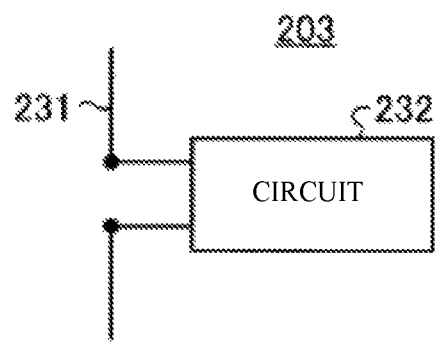
FIG. 5 is a diagram showing the configuration of the wireless communication device according to Embodiment 1 of the present invention.

FIG. 5 is a diagram showing the circuit configuration of the wireless communication device 203. The wireless communication device 203 includes: an antenna 231; and a circuit unit 232 connected to the antenna 231. The wireless communication device 203 receives a signal (carrier wave) transmitted by the transceiver 202, and using this signal as an energy source, returns a signal (reflection wave) to which information specific to the wireless communication device 203 is added.

The antenna 231 is connected to the circuit unit 232 and transmits and receives signals to and from the transceiver 202. The antenna 231 is a dipole antenna, and the impedance of the antenna is matched with the circuit unit 232. The antenna 231 may be a loop antenna, a patch antenna, or the like.

The circuit unit 232 includes the circuit 1. The circuit unit 232 is a digital circuit including a control circuit and a memory. When the control circuit receives a signal from the transceiver 202, the control circuit reads information stored in the memory, and returns a signal to the transceiver 202.

Figure 6:
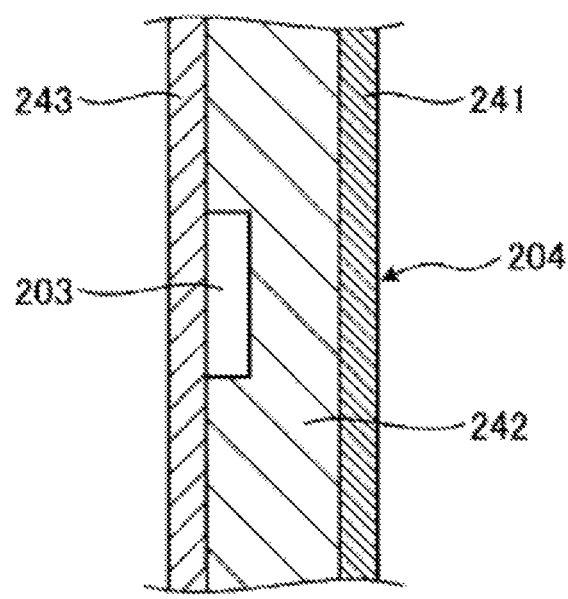
FIG. 6 is a partial sectional view showing the configuration of the main portion of the diaper according to Embodiment 1 of the present invention.

FIG. 6 is a partial sectional view showing the configuration of the main portion of the diaper 204. The diaper 204 is formed using a nonwoven fabric or the like, and includes: a surface material 241 which comes into direct contact with human skin; a water absorbent material 242 which is formed using a super absorbent polymer or the like, and which absorbs and retains moisture that has passed through the surface material 241; and a waterproof material 243 which is composed of a sheet-like material having waterproof properties, and which constitute an exterior body located on the outer surface side of the diaper 204, of the surfaces of the water absorbent material 242. The wireless communication device 203 is provided between the water absorbent material 242 and the waterproof material 243, and the water absorbent material 242 is in contact with at least a part of the wireless communication device 203. The wireless communication device 203 is preferably provided at a position at which the water absorbent material 242 more easily absorbs moisture at the time of urination, in other words, a position within the region which, when a person wears the diaper 204 and urinates, is more likely to get wet by the urine.

When a person wearing the diaper 204 having the above described configuration releases moisture out of the body, by urination and the like, the water absorbent material 242 absorbs the moisture. When the moisture absorbed by the water absorbent material 242 reaches the wireless communication device 203 and a detection part comes into contact with moisture, it causes changes in the properties of the detection part. The circuit unit 232 outputs a signal corresponding to the changes, and the antenna 231 transmits the signal to the transceiver 202. In cases where the 1-bit information included in the signal received from the wireless communication device 203 is different from that in the normal state, the transceiver 202 detects that moisture has attached to the wireless communication device 203. The transceiver 202 may have a function as a device for notifying that the diaper 204 is in contact with moisture, based on the information received. The moisture detection system 201, in this case, is a notification system which notifies that the diaper 204 is in contact with moisture. The device which notifies that the diaper 204 is in contact with moisture may be one other than the transceiver 202, and may be, for example, a speaker which notifies with a sound, a light source which notifies with light, or the like.

The antenna 231 may be attached at a position spaced apart from the attachment position of the circuit unit 232, because the antenna 231 is more likely to malfunction when the antenna gets wet, and also because the communication is more likely to be interfered by the presence of human body between the antenna 231 and the transceiver 202. For example, the antenna 231 may be attached on the ventral side of the human body, and the circuit unit 232 may be attached at a position where it gets wet upon urination. Further, the circuit unit 232 which detects moisture may be attached between the water absorbent material 242 and the waterproof material 243 so as to be in contact with the water absorbent material 242, and the antenna 231 may be attached on the outer surface of the waterproof material 243.

The detector 101, the wireless communication device 203 and the diaper 204 described above can also be formed using the circuit according to any of Embodiments 2 to 12 to be described later, and the same effect can be obtained.

According to Embodiment 1 of the present invention described above, it is possible to accurately detect not only the presence or absence of moisture, but also the amount of moisture in contact, with a simple and economically efficient configuration. Further, Embodiment 1 of the present invention eliminates the need for a conversion circuit for converting analog data to digital data. Still further, Embodiment 1 of the present invention allows for an easy and economically efficient production.

According to Embodiment 1 of the present invention, it is also possible to monitor the amount of moisture by the wireless communication device including the circuit, even from a location away from the wireless communication device.

Modified Example 1

Figure 7:
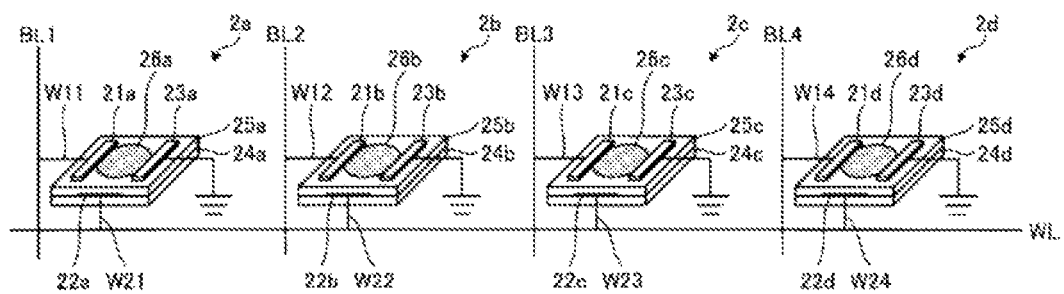
FIG. 7 is a diagram showing the configuration of the main portion of the circuit according to a modified example of Embodiment 1 of the present invention.

FIG. 7 is a diagram showing the configuration of the main portion of the circuit according to a modified example of Embodiment 1. This circuit is a memory. In the case of the configuration shown in FIG. 7, the transistors 2a to 2d, each having a function as a memory element, are arranged in the form of an array. The source electrodes 21a to 21d respectively included in the four transistors 2a to 2d are connected to wirings W11 to W14, respectively. The wirings W11 to W14 are connected to bit lines BL1 to BL4, respectively. The gate electrodes 22a to 22d respectively included in the transistor 2a to 2d are connected to a common word line WL, through wirings W21 to W24, respectively. The drain electrodes 23a to 23d respectively included in the transistors 2a to 2d are connected to the ground.

The transistors 2a to 2d, each having a function as a memory element, may constitute a memory array. This means that the information stored in the memory changes corresponding to the presence or absence of moisture.

Embodiment 2

The circuit according to Embodiment 2 of the present invention has the circuit structure shown in FIG. 1, as with the circuit according to Embodiment 1. In Embodiment 2, the insulating layers in the respective transistors contain materials different from each other.

The material to be used for forming a gate insulating layer is not particularly limited, and examples thereof include: inorganic materials such as silicon oxide and alumina; organic polymer materials such as polyimides, polyvinyl alcohol, polyvinyl chloride, polyethylene terephthalate, polyvinylidene fluoride, polysiloxanes and polyvinyl phenol (PVP); and mixtures of powders of inorganic materials and organic materials. Among these, one containing an organic compound containing a bond between a silicon atom and a carbon atom is preferred. Further, one containing an organic compound containing a bond between a silicon atom and a carbon atom, and a metal compound containing a bond between a metal atom and an oxygen atom is also preferred.

Examples of water-soluble resins include: homopolymers of polyethylene glycol, polyvinylpyrrolidone, polyvinyl alcohol, polyacrylamide, sodium polyacrylate, polyacrylic acid, polymethyl acrylate, polyethyl acrylate, polymethacrylic acid, poly-2-acrylamide-2-methylpropanesulfonic acid, sodium polystyrene sulfonate, polystyrene sulfonic acid, polyvinyl sulfonic acid, polyallylamine, polyethyleneimine, polyvinyl acetal, polyvinyl formal, poly(vinyl pyrrolidone), polylactic acid, polylactone, and the like; and copolymers containing these components. Examples also include methyl cellulose, carboxymethyl cellulose, hydroxyethyl cellulose and casein. Further, the water-soluble resin may also be, for example, a water-soluble polyester or a water-soluble polyurethane to which a hydrophilic group such as a carboxy group or a sulfone group is introduced.

Examples of water-absorbent resins include: a water-absorbent resin obtained by polymerization of starch or cellulose, a water-soluble monomer containing a hydrophilic group such as a carboxy group or a sulfone group and/or a monomer which becomes water-soluble by hydrolysis, and a crosslinking agent, as essential components, and carrying out hydrolysis as required; a hydrolyzate of a starch-acrylonitrile graft polymer; a hydrolyzate of a starch-acrylic acid graft polymer; a hydrolyzate of a cellulose-acrylonitrile graft polymer; a cross-linked product of carboxymethyl cellulose; a chitosan derivative; a hyaluronic acid derivative; a partial hydrolyzate of a cross-linked polyacrylamide; a cross-linked acrylic acid-acrylamide copolymer; a cross-linked sulfonated polystyrene; a saponified product of a vinyl ester-unsaturated carboxylic acid copolymer; a cross-linked polyacrylic acid (salt) such as sodium polyacrylate; a cross-linked acrylic acid-acrylic acid ester copolymer; an isobutylene-maleic anhydride copolymer; a cross-linked isobutylene-maleic anhydride copolymer such as sodium salt-cross-linked maleic anhydride; a cross-linked carboxylic acid-modified polyvinyl alcohol; a self-crosslinked polyacrylic acid salt; a cross-linked vinyl acetate-acrylic acid ester copolymer; and a nonionic polyalkylene oxide. The water-absorbent resin is not particularly limited, and conventionally known water-absorbent resins other than those mentioned above can also be used.

By mixing any of the above described materials to be used for forming a gate insulating layer, and a water-soluble resin and/or a water-absorbent resin to form a gate insulating layer, it is possible to form a gate insulating layer which shows responsiveness to moisture. Examples of the method of forming the gate insulating layer by mixing the material for forming the insulating layer and a water-soluble resin and/or a water-absorbent resin include a method of kneading these materials, and a method of chemically binding these materials. The insulating layer formed by mixing as described above dissolves or swells upon coming into contact with moisture, and destroys electrodes and the semiconductor layer formed on the insulating layer. As a result, the digital signal value read by the logic circuit changes from "0" to "1", or from "1" to "0".

For example, in FIG. 1, the insulating layers, which are provided below the wirings between the connecting points A to D and the transistors connected thereto, are configured to dissolve or swell upon contact with moisture, to cause a disconnection of the wirings. Further, the content(s) of the water-soluble resin and/or the water-absorbent resin in the gate insulating layers is/are varied, so that the insulating layers have varying degrees of responsiveness to moisture. By this arrangement, when moisture comes into contact the detector, the disconnection starts from the wiring on the gate insulating layer having a higher degree of responsiveness, and the current which has been flowing into the corresponding transistor starts to flow into the logic circuit. An increase in the current value is converted into the change from "0" to "1", and a signal sequence of (0,0,0,0) changes to (1,0,0,0), (1,1,0,0), (1,1,1,0) and (1,1,1,1), sequentially.

This is merely one example, and the circuit does not necessarily include four transistors in the same manner as in Embodiment 1, and the response does not necessarily proceed sequentially starting from the transistor on one end.

According to Embodiment 2 of the present invention described above, it is possible to obtain the same effect as that obtained in Embodiment 1.

Embodiment 3

Figure 8:
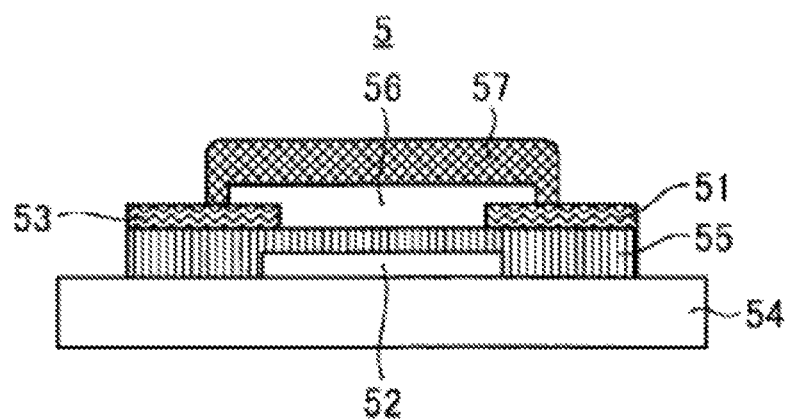
FIG. 8 is a sectional view showing the configuration of a transistor included in the circuit according to Embodiment 3 of the present invention.

The circuit according to Embodiment 3 of the present invention has the same circuit structure as the circuit according to Embodiment 1. In Embodiment 3, each transistor includes a second insulating layer. FIG. 8 is a sectional view showing the configuration of a transistor included in the circuit according to Embodiment 3 of the present invention. A transistor 5 shown in FIG. 8 includes a source electrode 51, a gate electrode 52, a drain electrode 53, a substrate 54, an insulating layer 55, a semiconductor layer 56 and a second insulating layer 57. The second insulating layer 57 is formed on the opposite side of the insulating layer 55, relative to the semiconductor layer 56. The expression "the opposite side of the insulating layer 55, relative to the semiconductor layer 56" refers to the upper side of the semiconductor layer 56, in cases where the insulating layer 55 is formed at the lower side of the semiconductor layer 56, as shown in FIG. 8. When the second insulating layers 57 in the respective transistors contain materials different from each other, the second insulating layers 57 show varying degrees of responsiveness to moisture.

Each second insulating layer may be a monolayer, or may be composed of a plurality of layers. Alternatively, one layer may be formed using a plurality of insulating materials, or may be formed by laminating layers made of a plurality of insulating materials.

The method of forming the second insulating layer is not particularly limited, and it is possible to use a dry method such as resistance heating vapor deposition, electron beam, sputtering or CVD. However, it is preferred to use an application method from the viewpoint of the production cost and a compatibility to a large area. The application method at least includes the step of applying a composition containing the polymer and the solvent to be contained in the second insulating layer, followed by drying. Specific examples of the application method which can be preferably used include: a spin coating method, a blade coating method, a slit die coating method, a screen printing method, a bar coater method, a casting method, a printing transfer method, a dip and pull method, an ink jet method and a drop casting method. Among these methods, the application method is preferably selected depending on the desired applied layer properties to be controlled, such as coating thickness, orientation, and the like.

Further, the thus formed applied layer may be subjected to an annealing treatment or hot blast drying in the atmosphere or under reduced pressure, or in an inert gas atmosphere such as a nitrogen or argon atmosphere. Specifically, the annealing may be carried out, for example, under the conditions of a temperature of from 50 to 150° C. for 3 to 30 minutes, under a nitrogen atmosphere. Such a drying step enables to thoroughly dry the applied layer, when the drying of the applied layer is insufficient.

In cases where the second insulating layers are used as detection parts, the second insulating layers may be configured, when the detector comes into contact with moisture, such that the second insulating layers dissolve and the ease of dissolution thereof varies between the transistors, or such that the ease of water penetration into the second insulating layers varies between the transistors. Alternatively, the second insulating layers may be configured to have a chemical structure which changes due to contact with moisture, and such that the chemical composition of the second insulating layers varies between the transistors. These methods enable the detection in multiple stages, corresponding to the amount of moisture.

In the case of varying the ease of dissolution of the second insulating layers, it can be achieved by forming each insulating layer by mixing a gate insulating layer material(s) and a water-soluble resin. In this case, the insulating layers varying in solubility can be formed by varying the contents of the components.

In the case of varying the ease of moisture penetration into the second insulating layers, it is considered possible to use a method of varying the chemical composition of the second insulating layers, such as, for example, imparting varying degrees of water repellency by incorporating a perfluoroalkyl group, or a method of varying the size and the number of pores, namely, varying the porosity, in the second insulating layers.

Each second insulating layer can be made to have a chemical composition which changes due to contact with moisture, for example, by a method of using a compound having a high reactivity with water, such as a carbamic acid derivative. The properties of each transistor are affected by whether a compound contained in the second insulating layer, which is in contact with the semiconductor layer, is an electron-donating compound or an electron-accepting compound. Therefore, the properties of the transistor when a carbamic acid derivative contained in the second insulating layer is in contact with the semiconductor layer, in the absence of water, are different from the properties of the transistor after the carbamic acid derivative has been converted to an amine due to contact with water, and this allows for varying the chemical composition between transistors.

Figure 9:
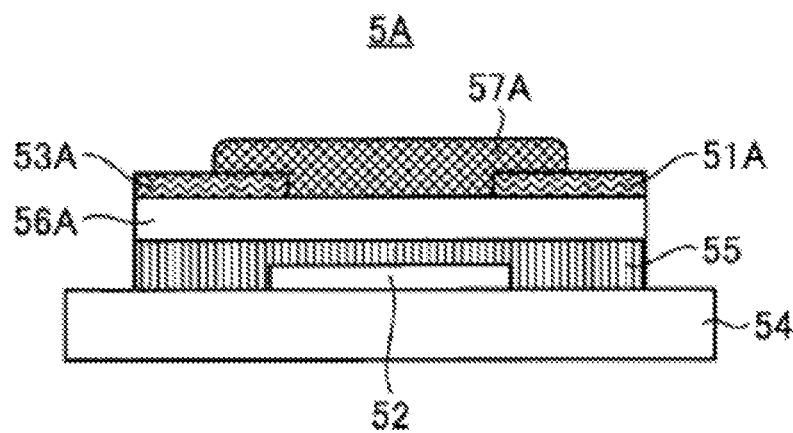
FIG. 9 is a sectional view showing the configuration of a transistor included in the circuit according to a modified example of Embodiment 3 of the present invention.

FIG. 9 is a sectional view showing the configuration of a transistor included in the circuit according to a modified example of Embodiment 3 of the present invention. A transistor 5A shown in FIG. 9 includes a source electrode 51A, agate electrode 52, a drain electrode 53A, a substrate 54, the insulating layer 55, a semiconductor layer 56A and a second insulating layer 57A. The second insulating layer 57A is formed on the opposite side of the insulating layer 55A, relative to the semiconductor layer 56A. The transistor 5A is different from the transistor 5 in that the source electrode 51A and the drain electrode 53A are laminated on the insulating layer 55.

According to Embodiment 3 of the present invention described above, it is possible to obtain the same effect as that obtained in Embodiment 1.

Embodiment 4

Figure 10:
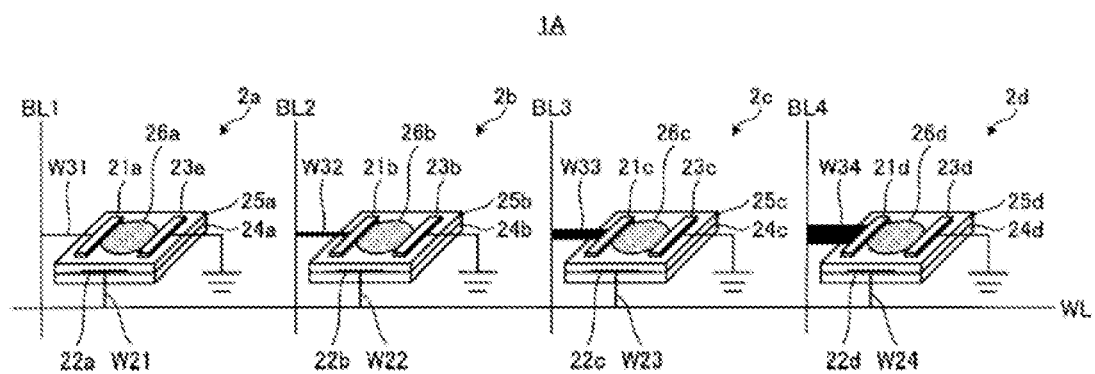
FIG. 10 is a diagram showing the configuration of the main portion of the circuit according to Embodiment 4 of the present invention.

FIG. 10 is a diagram showing the configuration of the main portion of the circuit according to Embodiment 4 of the present invention. The configuration of the circuit other than that shown in FIG. 10 is the same as that of Embodiment 1.

A circuit 1A shown in FIG. 10 is a memory, and four transistors 2a to 2d, each having a function as a memory element, are arranged in the form of an array. The source electrodes 21a to 21d respectively included in the four transistors 2a to 2d are connected to wirings W31 to W34, respectively. The wirings W31 to W34 are connected to the bit lines BL1 to BL4, respectively. The gate electrodes 22a to 22d respectively included in the four transistor 2a to 2d are connected to the common word line WL, through the wirings W21 to W24, respectively. The drain electrodes 23a to 23d respectively included in the four transistors 2a to 2d are connected to the ground.

The wirings W31 to W34 are formed using the same materials, and have thicknesses increasing in the order mentioned. Such a difference in thickness can be achieved, for example, by adjusting the amount of liquid used for forming the wirings by application, by an ink jet method.

The wiring W31 and W32 are composed of a water-soluble electrically conductive polymer. The water-soluble electrically conductive polymer is preferably an externally-doped polymer, rather than a self-doped polymer. Specifically, the water-soluble electrically conductive polymer may be, for example, at least one π-conjugated polymer selected from the group consisting of polyparaphenylene, polyphenylene vinylene, polyacetylene, polythiophene, polypyrrole, polyaniline, polyisothianaphthene, polyfuran, polycarbazole, polydiaminoanthraquinone and polyindole, which are unsubstituted or substituted, wherein the skeleton of the π-conjugated polymer contains a sulfonic acid group and/or a carboxy group, or an alkali metal salt, an ammonium salt or a substituted ammonium salt thereof; or contains an alkyl group or an alkyl group containing an ether bond, which is substituted with a sulfonic acid group and/or a carboxy group, or an alkali metal salt, an ammonium salt or a substituted ammonium salt thereof. A preferred example of such a water-soluble electrically conductive polymer may be, for example, a poly(3,4-ethylenedioxythiophene)-poly(styrenesulfonate) composite. The water-soluble electrically conductive polymer may also be, for example, a π-conjugated polymer having, on the nitrogen atom, an alkyl group or an alkyl group containing an ether bond, which is substituted with a sulfonic acid group and/or a carboxy group, or an alkali metal salt, an ammonium salt or a substituted ammonium salt thereof, or substituted with a sulfonic acid group and/or a carboxy group, or an alkali metal salt, an ammonium salt or a substituted ammonium salt thereof.

In the case of bottom-gate type transistors shown in FIG. 10, it is preferred that at least the wirings W31 to W34 which are more susceptible to coming into contact with moisture as compared to the wirings W21 to W24, be formed using the materials described above. In this case, the wirings W21 to W24 may be formed using an electrically conductive material. The wirings W21 to W24 are made of the same material and have the same thickness. In the case of using top-gate type transistors, in contrast, the wirings connected to the gate electrodes are more susceptible to coming into contact with moisture as compared to the wirings connected to the source electrodes. Therefore, it is preferred that at least the wirings W21 to W24 in FIG. 10 be formed using any of the materials described above. In this case, the wirings W31 to W34 may be formed using an electrically conductive material.

When the circuit 1A having the above described configuration comes into contact with moisture, a disconnection occurs in at least some of the wirings W31 to W34, depending on the amount of moisture, leading to an increase in resistance. In Embodiment 4 of the present invention, four wirings W31 to W34 have thicknesses different from each other, and thus have different threshold values for the amount of moisture at which the disconnection occurs. The wiring W31 having the smallest thickness has the minimum threshold value, and the wiring W34 having the largest thickness has the maximum threshold value. Accordingly, for example, in cases where the 4-bit information in the normal state, which is a state not in contact with moisture, is (1,1,1,1), the 4-bit information changes depending on the amount of moisture in contact, in the order from the smallest amount of moisture, specifically, from (1,1,1,1) to (0,1,1,1), (0,0,1,1), (0,0,0,1) and then to (0,0,0,0). As a result, based on the 4-bit information obtained from the detector according to Embodiment 4 of the present invention, it is possible to detect not only the presence or absence of contact with moisture but also the level of the amount of moisture, in the detector, in four stages.

According to Embodiment 4 of the present invention described above, it is possible to obtain the same effect as that obtained in Embodiment 1. Further, Embodiment 4 of the present invention enables to detect the amount of moisture in multiple stages, with a simple and economically efficient circuit configuration.

In addition to varying the thickness of the wirings W31 to W34, it is also possible to detect the level of the amount of moisture in four stages in the same manner as described above, for example, by increasing the width of the wirings in the order mentioned, by varying the porosity of the wirings, or the like. Further, it is also possible to obtain the same effect by varying the thickness, width, porosity or the like of the source electrodes or the drain electrodes, instead of the wirings.

In the above, a description has been given of the case in which the amount of moisture is detected in four stages. However, this is merely one example, and it is, of course, possible to achieve the detection of moisture in multiple stages in a manner corresponding to the number of transistors constituting the circuit.

In the case of using a plurality of top-gate type transistors, it is preferred to vary the thickness of the word lines connected to the gate electrodes of the respective transistors.

Modified Example 2

In Embodiments 1 to 4 and Modified Example 1, descriptions have been given using bottom-contact/bottom-gate type transistors. However, other types of transistors can also be used. The configurations of the transistors which can be used in the circuits described in the present specification will now be exemplified.

Figure 11:
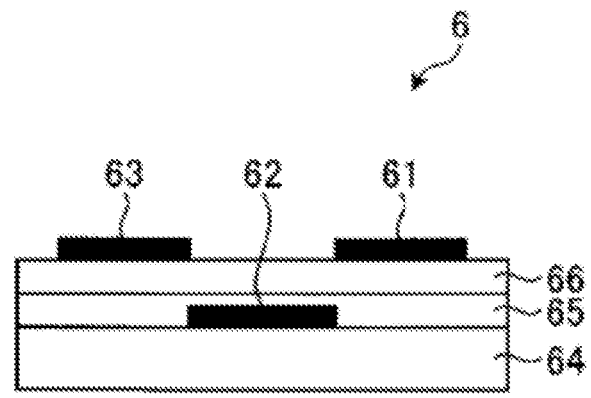
FIG. 11 is a sectional view showing the configuration of a top-contact/bottom-gate type transistor.

FIG. 11 is a sectional view showing the configuration of a top-contact/bottom-gate type transistor. A transistor 6 shown in FIG. 11 includes a source electrode 61, a gate electrode 62, a drain electrode 63, a substrate 64, an insulating layer 65 and a semiconductor layer 66.

Figure 12:
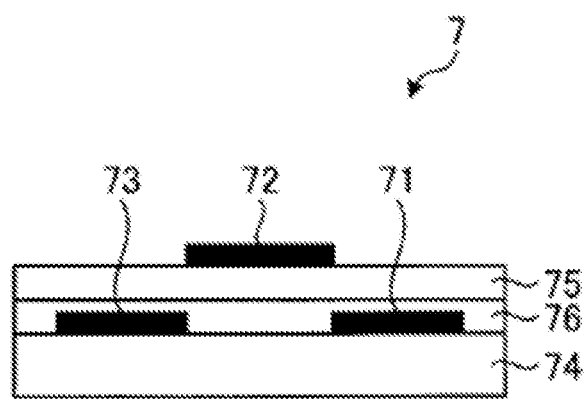
FIG. 12 is a sectional view showing the configuration of a bottom-contact/top-gate type transistor.

FIG. 12 is a sectional view showing the configuration of a bottom-contact/top-gate type transistor. A transistor 7 shown in FIG. 12 includes a source electrode 71, a gate electrode 72, a drain electrode 73, a substrate 74, an insulating layer 75 and a semiconductor layer 76.

Figure 13:
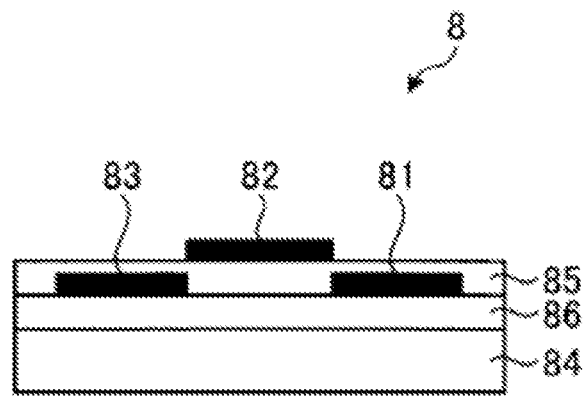
FIG. 13 is a sectional view showing the configuration of a top-contact/top-gate type transistor.

FIG. 13 is a sectional view showing the configuration of a top-contact/top-gate type transistor. A transistor 8 shown in FIG. 13 includes a source electrode 81, a gate electrode 82, a drain electrode 83, a substrate 84, an insulating layer 85 and a semiconductor layer 86.

It is also possible to use dual-gate type transistors in the circuits described in the present specification.

Embodiment 5

In Embodiment 5 of the present invention, the level of the amount of moisture is detected by configuring the wirings connecting between the respective resistance-transistor connections and the logic circuit (the wirings between the connecting points A to D and the logic circuit), in the circuit 1 shown in FIG. 1, to contain electrically conductive particles and a water-soluble resin. In Embodiment 5 of the present invention, each of the wirings as the component parts includes a detection part thereon.

Examples of the electrically conductive particles include particles of gold (Au), silver (Ag), copper (Cu), nickel (Ni), tin (Sn), bismuth (Bi), lead (Pb), zinc (Zn), palladium (Pd), platinum (Pt), aluminum (Al), tungsten (W), molybdenum (Mo) and carbon (C). In particular, the electrically conductive particles containing at least one element selected from the group consisting of gold, silver, copper, nickel, tin, bismuth, lead, zinc, palladium, platinum, aluminum and carbon, are preferred.

As the water-soluble resin, any of those mentioned above can be used.

When the wirings having the above described configuration come into contact with moisture, the water-soluble resin contained therein is dissolved to cause changes in the composition of the wirings, resulting in an increase in the electrical resistance. By setting in advance the resistance values of the resistances in the circuit such that currents flow into the logic circuit, the 1-bit information to be read by the logic circuit from each of the connecting points A to D changes, when the electrical resistance is increased in the wirings.

Varying degrees of responsiveness to moisture can be achieved by varying the content of the water-soluble resin in the wirings or by varying the shape of the wirings.

Although the wirings connecting the connecting points A to D and the logic circuit are used as an example, here, the configuration is not limited thereto. The wirings between the connecting points A to D and the transistors may be configured to contain electrically conductive particles and a water-soluble resin. Alternatively, the word line, the bit lines, the wirings connecting between the word line and the gate electrodes, the wirings connecting between the bit lines and the source electrodes or the drain electrodes, or the like, of the transistors formed in the form of an array may also be configured in the same manner.

According to Embodiment 5 of the present invention described above, it is possible to obtain the same effect as that obtained in Embodiment 1.

Embodiment 6

In Embodiment 6 of the present invention, the wirings connecting between the connecting points A to D and the transistors, in the circuit 1 shown in FIG. 1, are configured to contain electrically conductive particles and a water-absorbent resin. This configuration also enables to accurately detect the level of the amount of moisture. Specifically, in a state not in contact with moisture, a current flows between each of the connecting points A to D and each transistor, and thus the current does not flow to the logic circuit, resulting in a signal value of "0". Upon coming into contact with moisture, the water-absorbent resin in each wiring absorbs moisture, and this causes the wiring containing the electrically conductive particles and the water-absorbent resin to swell, leading to an increase in the resistance of the wiring or a substantial disconnection. As a result, the current starts to flow to the logic circuit, changing the signal value to "1". In Embodiment 6 of the present invention, each of the wirings as the component parts includes a detection part thereon.

As the electrically conductive particles and the water-absorbent resin, any of the above described materials can be used. Varying degrees of responsiveness to moisture can be achieved by varying the content of the water-absorbent resin in the wirings or by varying the shape of the wirings.

According to Embodiment 6 of the present invention described above, it is possible to obtain the same effect as that obtained in Embodiment 1.

Embodiment 7

In Embodiment 7 of the present invention, the wirings connecting between the connecting points A to D and the transistors, in the circuit 1 shown in FIG. 1, are configured to contain electrically conductive particles and a water-soluble electrically conductive polymer. This configuration also enables to detect the level of the amount of moisture in stages. Specifically, in a state not in contact with moisture, a current flows between each of the connecting points A to D and each transistor, and thus the current does not flow to the logic circuit, resulting in a signal value of "0". Upon coming into contact with moisture, the water-soluble electrically conductive polymer in each wiring is dissolved to cause a disconnection. As a result, the current starts to flow to the logic circuit, changing the signal value to "1". In Embodiment 7 of the present invention, as well, each of the wirings as the component parts includes a detection part thereon.

The water-soluble electrically conductive polymer is preferably an externally-doped polymer, rather than a self-doped polymer. Specifically, the water-soluble electrically conductive polymer may be, for example, at least one n-conjugated polymer selected from the group consisting of polyparaphenylene, polyphenylene vinylene, polyacetylene, polythiophene, polypyrrole, polyaniline, polyisothianaphthene, polyfuran, polycarbazole, polydiaminoanthraquinone and polyindole, which are unsubstituted or substituted, wherein the skeleton of the n-conjugated polymer contains a sulfonic acid group and/or a carboxy group, or an alkali metal salt, an ammonium salt or a substituted ammonium salt thereof; or contains an alkyl group or an alkyl group containing an ether bond, which is substituted with a sulfonic acid group and/or a carboxy group, or an alkali metal salt, an ammonium salt or a substituted ammonium salt thereof. A preferred example of such a water-soluble electrically conductive polymer may be, for example, a poly(3,4-ethylenedioxythiophene)-poly (styrenesulfonate) composite. The water-soluble electrically conductive polymer may also be, for example, a π-conjugated polymer having, on the nitrogen atom, an alkyl group or an alkyl group containing an ether bond, which is substituted with a sulfonic acid group and/or a carboxy group, or an alkali metal salt, an ammonium salt or a substituted ammonium salt thereof, or substituted with a sulfonic acid group and/or a carboxy group, or an alkali metal salt, an ammonium salt or a substituted ammonium salt thereof.

According to Embodiment 7 of the present invention described above, it is possible to obtain the same effect as that obtained in Embodiment 1.

Modified Example 3

In the case of a bottom-gate type transistor shown in FIG. 2A or FIG. 11, it is preferred that at least the wiring connected to the source electrode or the drain electrode, which is more susceptible to coming into contact with moisture as compared to the wiring connected to the gate electrode, be formed using the above described water-soluble electrically conductive polymer. In this case, the wiring connected to the gate electrode may be formed using an electrically conductive material. In the case of a top-gate type transistor, the wiring connected to the gate electrode is more susceptible to coming into contact with moisture, as compared to the wiring connected to the source electrode or the drain electrode. Therefore, at least the wiring connected to the gate electrode is preferably formed using the above described water-soluble electrically conductive polymer, and the wiring connected to the source electrode and the wiring connected to the drain electrode may be formed using an electrically conductive material.

Embodiment 8

Figure 14:
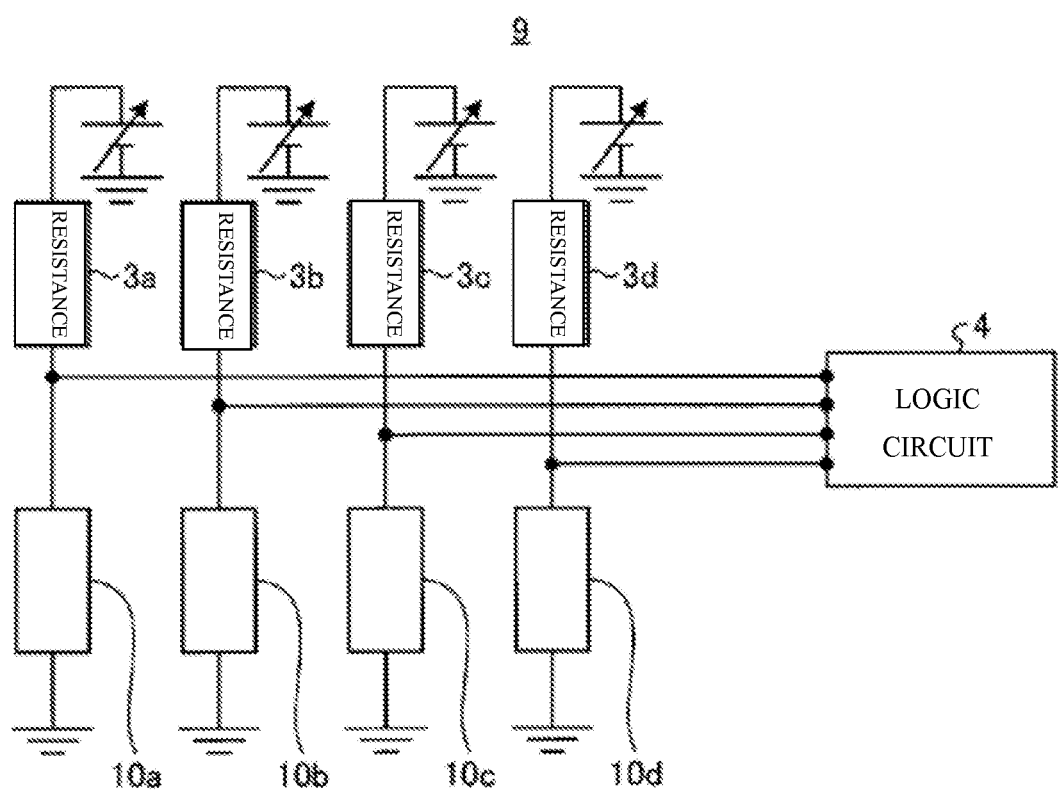
FIG. 14 is a diagram showing the configuration of the circuit according to Embodiment 8 of the present invention.

Embodiment 8 of the present invention is characterized in that a plurality of resistances are provided in the circuit, and changes in multiple stages are provided based on the responses therefrom. In other words, in Embodiment 8 of the present invention, each of the resistances as the component parts includes a detection part. FIG. 14 is a diagram showing the configuration of the circuit according to Embodiment 8 of the invention. A circuit 9 shown in FIG. 14 includes resistances 10a to 10d each including a detection part, instead of the transistors 2a to 2d in the circuit 1 shown in FIG. 1. The resistances 10a to 10d can be formed using, for example, the electrically conductive particles and the water-soluble resin, the electrically conductive particles and the water-absorbent resin, or the water-soluble electrically conductive polymer, as described above. By this arrangement, it is possible to further clarify the changes in the signal values upon coming into contact with moisture.

The resistances 10a to 10d may be provided at any locations as long as the changes in the current values can be clearly seen. In addition to the configuration shown in FIG. 14, it is also possible to provide the resistances, for example, somewhere in the wirings to which the responsiveness to moisture has been imparted, in any of Embodiments 5 to 7.

According to Embodiment 8 of the present invention described above, it is possible to obtain the same effect as that obtained in Embodiment 1. Further, the responsiveness to moisture is further improved, and the changes in the signal values upon detection of moisture are more clarified.

Embodiment 9

Figure 15:
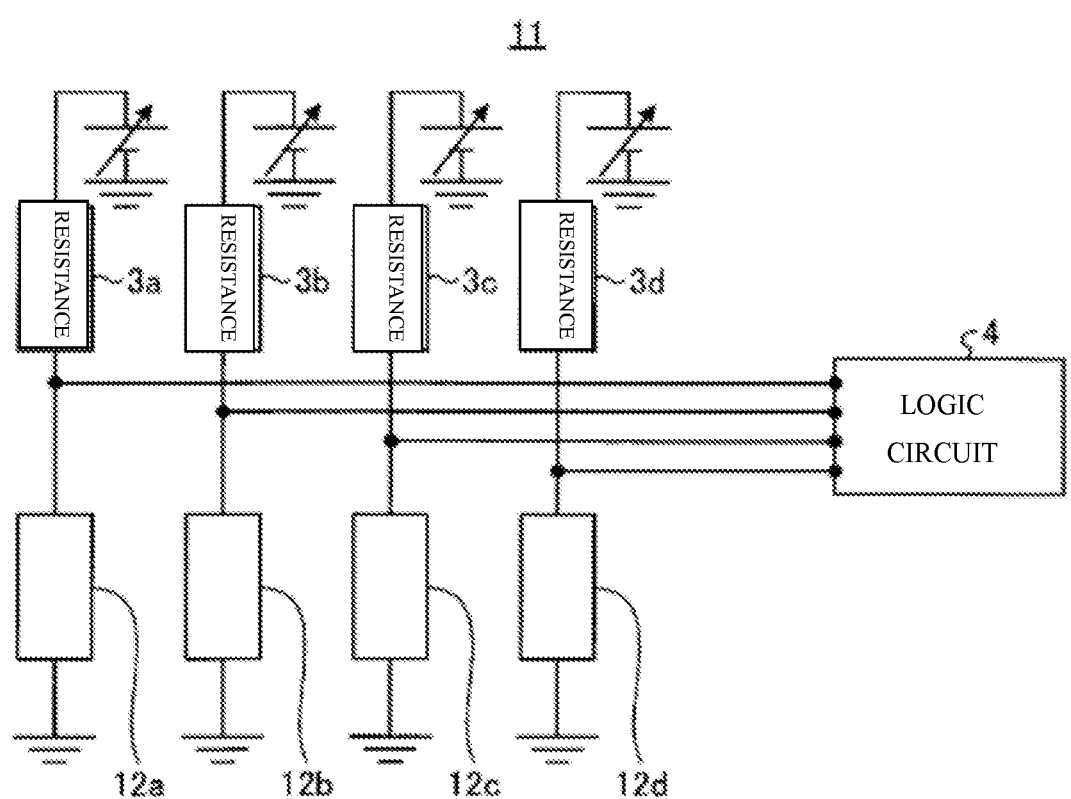
FIG. 15 is a diagram showing the configuration of the circuit according to Embodiment 9 of the present invention.

FIG. 15 is a diagram showing the configuration of the circuit according to Embodiment 9 of the present invention. A circuit 11 shown in FIG. 15 includes diodes 12a to 12d as the component parts, instead of the transistors 2a to 2d of the circuit 1 shown in FIG. 1. In Embodiment 9 of the present invention, the diodes 12a to 12d each includes a detection part. In this case, in a state not in contact with moisture, a current flows to each diode, and thus the current does not flow to the logic circuit, resulting in a signal value of "0". Upon coming into contact with moisture, the properties of each diode change. As a result, the current starts to flow to the logic circuit, changing the signal value to "1".

By varying the ease of change in the properties of the diodes at this time, namely, by varying the threshold value between the diodes, changes in the properties of the diodes occur sequentially, thereby enabling to detect the amount of moisture in stages. This can be achieved by varying the properties of the insulating layers or the second insulating layers which are in contact with the semiconductors used in the diodes, as described above.

The diodes each includes, for example, a pair of electrodes provided on the surface of an insulating substrate, and a semiconductor layer formed between the pair of electrodes. The semiconductor layer contains, for example, a carbon nanotube. The configuration of the diode is not particularly limited, and other configurations are disclosed, for example, in WO 2016/158862.

Figure 16:
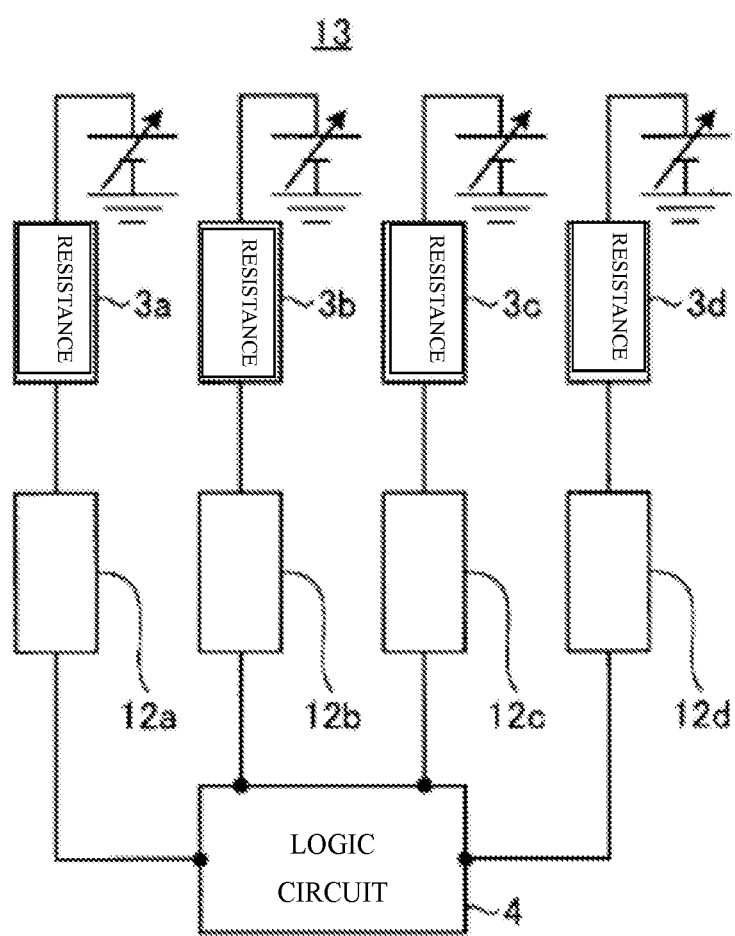
FIG. 16 is a diagram showing the configuration of the circuit according to a modified example of Embodiment 9 of the present invention.

In Embodiment 9 of the present invention, the logic circuit 4 may be directly connected to each of the diodes 12a to 12d, as in a circuit 13 shown in FIG. 16. In this case, as well, the signal value to be output is "1" when not in contact with moisture, which is a state in which a current flows. Upon coming into contact with moisture, the current ceases to flow, changing the signal value to "0".

According to Embodiment 9 of the present invention described above, it is possible to obtain the same effect as that obtained in Embodiment 1.

Embodiment 10

Figure 17:
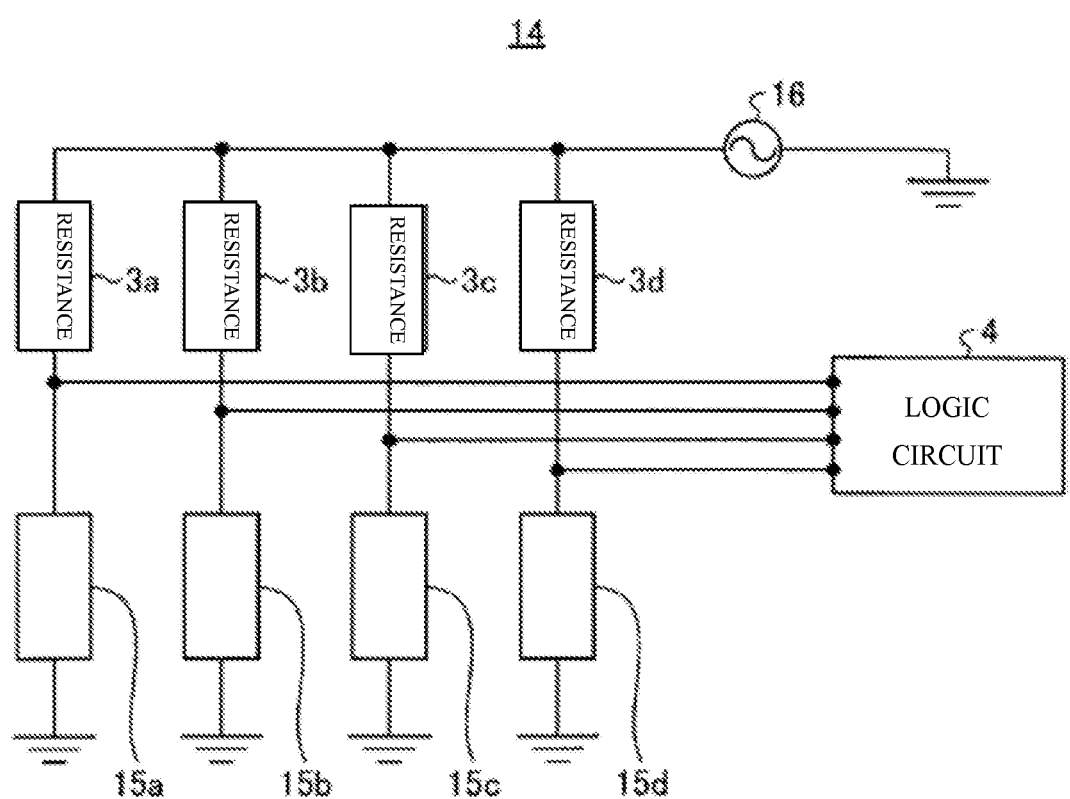
FIG. 17 is a diagram showing the configuration of the circuit according to Embodiment 10 of the present invention.

FIG. 17 is a diagram showing the configuration of the circuit according to Embodiment 10 of the present invention. A circuit 14 shown in FIG. 17 includes capacitors 15a to 15d as the component parts, instead of the transistors 2a to 2d of the circuit 1 shown in FIG. 1. In Embodiment 10 of the present invention, the capacitors 15a to 15d each includes a detection part. A capacitor is also referred to as a condenser. The sides of the resistances 3a to 3d which are not connected to the capacitors 15a to 15d are connected to an AC power supply 16. In Embodiment 10 of the present invention, each of the capacitors includes a detection part.

When the AC power supply 16 applies a square wave voltage to the resistances 3a to 3d, the phase of the currents flowing through the resistances 3a to 3d shifts from the phase of the applied voltage, by the action of the capacitors 15a to 15d. The shift in the phase of the circuit 14 varies depending on the dielectric constant of a dielectric in each capacitor connected to each resistance. The time constant at this time is the product of the resistance value of the resistance and the electrostatic capacity of the capacitor connected to the resistance. In Embodiment 10 of the present invention, each capacitor is formed using a dielectric whose dielectric constant changes due to contact with moisture. Further, in a state not in contact with moisture, each capacitor is configured to output a signal value of "1" by allowing a current to flow following the square wave. In the circuit 14 having such a configuration, when the capacitor which is in contact with moisture becomes unable to follow the square wave, due to changes in the dielectric constant, the current value is reduced to be equal to or lower than the threshold value of the logic circuit 4, and as a result, the signal value changes to "0". It is also possible, in principle, to configure each capacitor such that, when the capacitor comes into contact with water and moisture infiltrates into the dielectric, the signal value to be output by the capacitor changes from "0" to "1".

Examples of the dielectric include: metal oxides such as tantalum oxide (such as $Ta_2O_5$), aluminum oxide (such as $Al_2O_3$), silicon oxide (such as $SiO_2$), zirconium oxide (such as $ZrO_2$), titanium oxide (such as $TiO_2$), yttrium oxide (such as $Y_2O_3$), lanthanum oxide (such as $La_2O_3$) and hafnium oxide (such as $HfO_2$); metal nitrides such as tantalum nitride (such as TaN), aluminum nitride (such as AlN), silicon nitride (such as $Si_3N_4$), zirconium nitride (such as ZrN), titanium nitride (such as TiN), yttrium nitride (such as YN), lanthanum nitride (such as LaN) and hafnium nitride (such as HfN); and oxides of two or more kinds of metals such as barium titanate ($BaTiO_3$), strontium titanate ($SrTiO_3$) and calcium titanate ($CaTiO_3$).

Examples of organic dielectrics include polyethylene, polyesters, polyimides, polyphenylene sulfide, organic glasses, polyvinyl alcohol, polyvinyl phenol, polyparaxylene, polyacrylonitrile, polyacrylic acid derivatives and polymethacrylic acid derivatives. An inorganic or an organic dielectric may be used singly, or two or more kinds thereof may be used in combination.

According to Embodiment 10 of the present invention described above, it is possible to obtain the same effect as that obtained in Embodiment 1.

Embodiment 11

Figure 18:
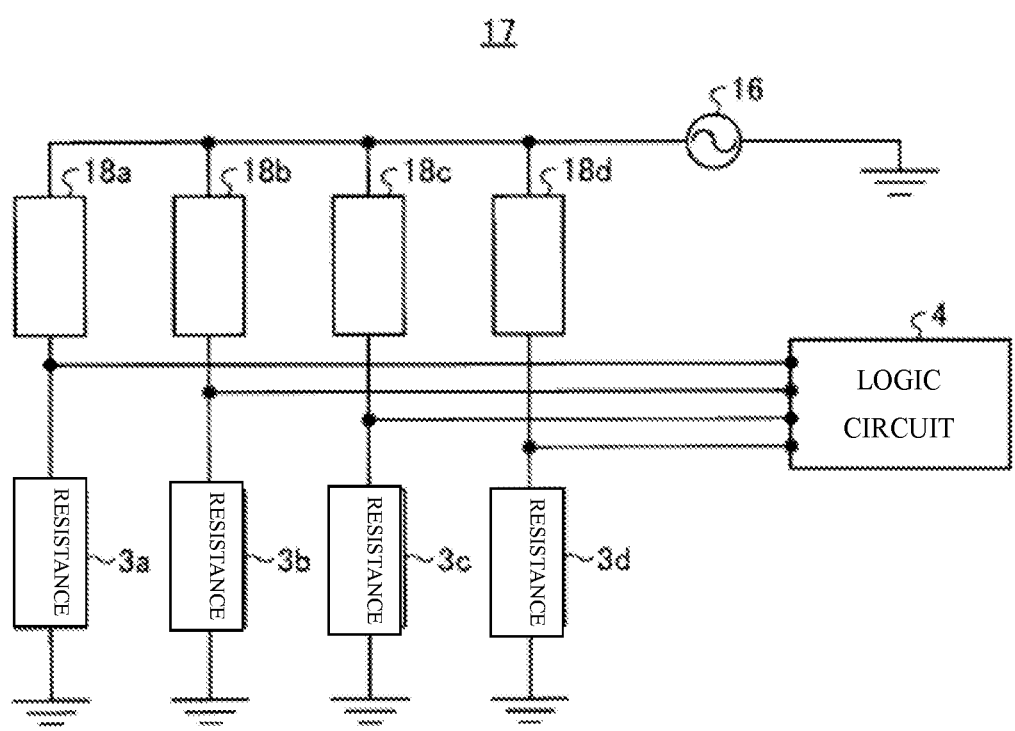
FIG. 18 is a diagram showing the configuration of the circuit according to Embodiment 11 of the present invention.

FIG. 18 is a diagram showing the configuration of the circuit according to Embodiment 11 of the present invention. A circuit 17 shown in FIG. 18 includes inductors 18a to 18d as the component parts, instead of the resistances 3a to 3d in the circuit 14 shown in FIG. 17, respectively, and includes the resistances 3a to 3d as the component parts, instead of the capacitors 15a to 15d in the circuit 14, respectively. An inductor is also referred to as a coil or a reactor. In Embodiment 11 of the present invention, the inductors 18a to 18d each includes a detection part.

When the center conductor of each inductor is formed using, for example, the electrically conductive particles and the water-soluble resin, the electrically conductive particles and the water-absorbent resin, or the water-soluble electrically conductive polymer, as described above, the contact with moisture causes changes in magnetic permeability in the inductor. As a result, upon coming into contact with moisture, each inductor outputs a signal value different from the signal value to be output when the inductor is not in contact with moisture. Specifically, for example, when the inductor which has been outputting a signal value of "1" in a state not in contact with moisture, becomes unable to follow the square wave due to changes in the magnetic permeability, the current value is reduced to be equal to or lower than the threshold value of the logic circuit 4, and as a result, the signal value to be output by the inductor changes to "0". It is also possible, in principle, to configure each inductor such that, when water comes into contact with, and infiltrates into, the center conductor of the inductor, the signal value to be output by the inductor changes from "0" to "1".

According to Embodiment 11 of the present invention described above, it is possible to obtain the same effect as that obtained in Embodiment 1.

Embodiment 12

Embodiment 12 of the present invention has the same configuration as that of Embodiment 2. Embodiment 12 of the present invention is different from Embodiment 2 in that the insulating layer in each transistor further contains, as a photosensitive organic component, an addition reaction product of a radically polymerizable compound.

The radically polymerizable compound refers to a compound containing a plurality of ethylenically unsaturated double bonds within the molecule. By the irradiation of ultraviolet (UV) light, radicals generated from a photopolymerization initiator to be described later causes the radical polymerization of the radically polymerizable compound to proceed. This leads to an improvement in the crosslinking density of the insulating layer, as a result of which the hardness of the insulating layer can be improved.

The radically polymerizable compound is preferably a compound containing a (meth)acrylic group, in which the radical polymerization more easily proceeds. From the viewpoint of improving the sensitivity during the irradiation of UV light and improving the hardness of the insulating layer, the radically polymerizable compound is more preferably a compound containing two or more (meth)acrylic groups within the molecule.

From the viewpoint of improving the sensitivity during the irradiation of UV light and improving the crack resistance of the resulting cured film, the radically polymerizable compound is preferably trimethylolpropane tri(meth)acrylate, ditrimethylolpropane tetra(meth)acrylate, pentaerythritol tetra(meth)acrylate, dipentaerythritol penta(meth)acrylate, dipentaerythritol hexa(meth)acrylate, tripentaerythritol octa(meth)acrylate, 1,3,5-tris((meth)acryloxyethyl)isocyanuric acid or 9,9-bis[4-(2-(meth)acryloxyethoxy)phenyl]fluorene; or an acid-modified product thereof. Further, the radically polymerizable compound is also preferably an ethylene oxide-modified product or a propylene oxide-modified product, from the viewpoint of improving the sensitivity during the irradiation of UV light and improving the crack resistance of the resulting cured film.

The insulating layer may further contain, as a photosensitive organic component, a compound (hereinafter, referred to as "photopolymerization initiator") which undergoes bond cleavage and/or a reaction due to the irradiation of UV light, and generates radicals. The incorporation of the photopolymerization initiator allows the radical polymerization of the above described radically polymerizable compound to proceed, thereby enabling to facilitate the addition reaction during the irradiation of UV light. For example, the photopolymerization initiator is preferably a benzyl ketal-based photopolymerization initiator, an α-hydroxyketone-based photopolymerization initiator, an α-aminoketone-based photopolymerization initiator, an acylphosphine oxide-based photopolymerization initiator, an oxime ester-based photopolymerization initiator, an acridine-based photopolymerization initiator, a titanocene-based photopolymerization initiator, a benzophenone-based photopolymerization initiator, an acetophenone-based photopolymerization initiator, an aromatic ketoester-based photopolymerization initiator or a benzoic acid ester-based photopolymerization initiator. From the viewpoint of improving the sensitivity during the irradiation of UV light, the photopolymerization initiator is more preferably an α-hydroxyketone-based photopolymerization initiator, an α-aminoketone-based photopolymerization initiator, an acylphosphine oxide-based photopolymerization initiator, an oxime ester-based photopolymerization initiator, an acridine-based photopolymerization initiator or a benzophenone-based photopolymerization initiator. The photopolymerization initiator is still more preferably an α-aminoketone-based photopolymerization initiator, an acylphosphine oxide-based photopolymerization initiator or an oxime ester-based photopolymerization initiator. Specific examples of the photopolymerization initiator include 1-[4-(phenylthio)phenyl]octane-1,2-dione-2-(O-benzoyl)oxime and 1-[9-ethyl-6-(2-methylbenzoyl)-9H-carbazol-3-yl]ethanone-1-(O-acetyl)oxime, which are oxime ester-based photopolymerization initiators. However, other known materials can also be used.

The insulating layer may further contain, as a photosensitive organic component, a compound (hereinafter, referred to as "photoacid generator") which generates an acid when irradiated with light. Examples of the photoacid generator include an onium salt compound, a halogen-containing compound, a diazoketone compound, a diazomethane compound, a sulfone compound, a sulfonic acid ester compound and a sulfonimide compound. Specific examples of the diazoketone compound include a 1,3-diketo-2-diazo compound, a diazobenzoquinone compound and a diazonaphthoquinone compound. Among these, a diazonaphthoquinone compound is preferred, from the viewpoint of improving the patterning accuracy and improving the crack resistance of the insulating layer. Examples of preferred diazoketone compounds include an ester of 1,2-naphthoquinonediazide-4-sulfonic acid with 2,2,3,4,4'-pentahydroxybenzophenone, and an ester of 1,2-naphthoquinonediazide-4-sulfonic acid with 1,1,1-tris(4-hydroxyphenyl)ethane.

The photopolymerization initiator and the photoacid generator are preferably used in combination with a sensitizer, which is a photosensitive organic component. The sensitizer does not cause coloration in a photobleaching reaction, and thus is capable of achieving a higher sensitivity while retaining a high transparency, even in the insulating layer. The sensitizer is not particularly limited, and a known material can be used. However, a 9,10-disubstituted anthracene compound is particularly preferred.

The insulating layer may further contain, as a photosensitive organic component, an addition reaction product of a chain transfer agent. The chain transfer agent refers to a compound capable of receiving a radical from the growth terminal of a polymer chain which is obtained by radical polymerization during the irradiation of UV light, and mediating the transfer of the radical to another polymer chain. The incorporation of a chain transfer agent enables to improve the sensitivity during the irradiation of UV light. This is assumed to be because radicals generated by the irradiation of UV light are transferred to other polymer chains by the chain transfer agent, as a result of which radical cross-linking extends deeply into the film. The chain transfer agent is preferably a thiol-based chain transfer agent.

The insulating layer may further contain, as a photosensitive organic component, a polymerization inhibitor. The polymerization inhibitor refers to a compound capable of capturing a radical generated during the irradiation of UV light, or a radical at the growth terminal of a polymer chain which is obtained by radical polymerization during the irradiation of UV light, and retaining the radical as a stabilized radical, thereby terminating the radical polymerization. The incorporation of an adequate amount of polymerization inhibitor enables to prevent the generation of an excessive amount of radicals during the irradiation of UV light, and to control the radical polymerization. The polymerization inhibitor is preferably a phenol-based polymerization inhibitor.

The insulating layer may further contain, in addition to a polymer to which inorganic particles are bound, inorganic particles to which no polymer is bound. Preferred materials and shape of the inorganic particles to which no polymer is bound, are the same as those of the case in which a polymer is bound, as described above.

If necessary, the insulating layer may contain a viscosity modifier, a surfactant, a stabilizer, and/or the like. Further, the insulating layer may contain a residual solvent. Examples of the surfactant include a fluorochemical surfactant, a silicone-based surfactant, a polyalkylene oxide-based surfactant and an acrylic surfactant. Specific examples of the fluorochemical surfactant include MEGAFACE F142D, MEGAFACE F172, MEGAFACE F173 and MEGAFACE F183 (all of the above manufactured by DIC Corporation); and NBX-15, FTX-218 and DFX-18 (manufactured by NEOS Company Limited). Specific examples of the silicone-based surfactant include BYK-333 (manufactured by BYK Japan KK).

In Embodiment 12 of the present invention, each transistor is formed using a thin film transistor including an insulating layer containing a photosensitive organic matter, and this makes it possible to selectively form vias by photolithography. Therefore, for example, when vias are selectively formed in the regions of the insulating layer at which the wirings come into contact, and a film composed of a water-soluble resin (water-soluble resin film) is formed in each of the vias by an application method, such as an ink jet method or a dispenser method, the water-soluble resin film dissolves upon coming into contact with moisture. This causes the disconnection of the wiring which is in contact with the corresponding water-soluble resin film, resulting in an increase in the resistance. It is also possible to form a film composed of a water-absorbent resin (water-absorbent resin film), instead of the water-soluble resin film, in each of the vias in the insulating layer, by a coating method in the same manner as described above. In this case, when the water-absorbent resin film comes into contact with moisture, the water-absorbent resin film swells, and this causes the disconnection of the wiring which is in contact with the corresponding water-absorbent resin film.

According to Embodiment 12 of the present invention described above, it is possible to obtain the same effect as that obtained in Embodiment 1.

Other Embodiments

As described above, the present invention has been described with reference to some examples. However, the embodiments of the present invention are not limited to those described above, and each detection part may be provided in another location, such as in a thyristor or the like.

It is noted that, in the case of a wireless communication device, the power supply in the circuit diagram of any of the above described embodiments or modified examples corresponds to an antenna. If necessary, the electromagnetic wave received by the antenna can be converted to a direct current by a rectifier circuit. Further, the above described wireless communication device may be an active-type wireless communication device including a built-in battery.

The circuit according to the present invention can also be applied in a submersion test of an automobile. In this case, the circuit according to the present invention is pasted on a door portion or the like of an automobile, to be subjected to a submersion test. After the submersion test, it is possible to confirm the occurrence of a slight infiltration of moisture into the interior of the automobile, by reading the digital signal sequence of the circuit which had been pasted on the automobile.

As described above, the present invention can include various embodiments and the like which have not been described herein.

INDUSTRIAL APPLICABILITY

The circuit according to the present invention and a detector including the same has a simple and economically efficient configuration, and can be used not only the diaper and the submersion test of an automobile as described above, but also in a system for detecting water leaks in equipment such as piping or in infrastructure such as bridges, tunnels and dams, and the like.

REFERENCE SIGNS LIST 1, 1A, 9, 11, 13, 14, 17 circuit
2a to 2d, 5, 5A, 6, 7, 8 transistor
3a to 3d, 10a to 10d resistance
4 logic circuit
12a to 12d diode
15a to 15d capacitor
16 AC power supply
18a to 18d inductor
21a to 21d, 51, 51A, 61, 71, 81 source electrode
22a to 22d, 52, 62, 72, 82 gate electrode
23a to 23d, 53, 53A, 63, 73, 83 drain electrode
24a, 54, 64, 74, 84 substrate
25a, 55, 55A, 65, 75, 85 insulating layer
26a, 56, 56A, 66, 76, 86 semiconductor layer
57, 57A second insulating layer
101 detector
102 recognition unit
201 moisture detection system
202 transceiver
203 wireless communication device
231 antenna
232 circuit unit
241 surface material
242 water absorbent material
243 waterproof material
BL1 to BL4 bit line
W11 to W14, W21 to W24, W31 to W34 wiring
WL word line

The invention claimed is:
1. A circuit comprising a plurality of component parts formed on a substrate and having common functions,
wherein said plurality of component parts each comprises a detection part which shows responsiveness to moisture;

wherein said responsiveness to moisture varies between said plurality of component parts; and wherein the presence or absence of a response to moisture detected by each detection part corresponds to a binary digital signal, and whereby said circuit outputs a sequence of binary digital signals.

2. The circuit according to claim 1, wherein a plurality of said detection parts have chemical compositions different form each other, and thus have varying degrees of responsiveness to moisture.

3. The circuit according to claim 1, wherein a plurality of said detection parts have structures different form each other, and thus have varying degrees of responsiveness to moisture.

4. The circuit according to claim 1, wherein said component parts are each at least one selected from the group consisting of a transistor, a resistance, a diode, a capacitor, an inductor, a thyristor, and a wiring.

5. The circuit according to claim 1, wherein said component parts are each a transistor.

6. The circuit according to claim 5, wherein said transistor comprises:
a first electrode;
a second electrode;
an insulating layer; and
a third electrode electrically insulated from said first electrode and said second electrode by said insulating layer;
wherein at least some of a plurality of said transistors each includes a semiconductor layer between said first electrode and said second electrode; and
wherein said detection part is at least one selected from the group consisting of said first electrode, said second electrode, said third electrode, said insulating layer and said semiconductor layer.

7. The circuit according to claim 6, wherein said insulating layer comprises a water-soluble resin and/or a water-absorbent resin.

8. The circuit according to claim 7, wherein said insulating layer comprises a photosensitive organic compound.

9. The circuit according to claim 5, wherein said transistor comprises:
a semiconductor layer;
an insulating layer; and
a second insulating layer formed on the opposite side of said insulating layer, relative to said semiconductor layer;
wherein said detection part is said second insulating layer.

10. The circuit according to claim 1, comprising:
a memory array in which a plurality of transistors each electrically connected to wirings are arranged in the form of an array; and
a control circuit which reads information from said plurality of transistors and outputs the information;
wherein said detection part is provided in each transistor or in each wiring in said memory array; and
wherein the information to be read from said memory array varies depending on the presence or absence of contact between the said detection part and moisture.

11. The circuit according to claim 1, comprising:
a plurality of transistors which are each electrically connected to wirings, and are arranged in the form of an array; and
a control circuit which reads information from said plurality of transistors and outputs the information;
wherein at least one of the thickness and the width of a plurality of said wirings connected to said plurality of transistors varies between said wirings, and said wirings each includes said detection part.

12. The circuit according to claim 5, wherein said semiconductor layer in said transistor comprises at least one selected from the group consisting of fullerene, carbon nanotubes, graphene and carbon nanohorns.

13. The circuit according to claim 1, wherein said detection part is at least a part of said wiring; and
wherein said wiring comprises electrically conductive particles and a water-soluble resin and/or a water-absorbent resin, or said wiring comprises a water-soluble electrically conductive polymer.

14. The circuit according to claim 1, wherein said detection part is at least a part of said resistance; and
wherein said resistance comprises electrically conductive particles and at least one selected from the group consisting of a water-soluble resin, a water-absorbent resin, and a water-soluble electrically conductive polymer.

15. A detector comprising the circuit according to claim 1.

16. A wireless communication device comprising:
the circuit according to claim 1; and
an antenna which is connected to said circuit and which transmits and receives signals to and from a transceiver in a non-contact manner.

17. A moisture detection system comprising:
the wireless communication device according to claim 16; and
a transceiver which is capable of communicating with said wireless communication device in a non-contact manner, and which detects the presence or absence of contact between the wireless communication device with moisture and/or the amount of moisture in contact, based on the signal returned in response to the signal transmitted to the wireless communication device.

18. A diaper comprising:
a water absorbent material which absorbs and retains moisture; and
a waterproof material having a waterproof function and covering said water absorbent material;
wherein said diaper is capable of being attached to a human body and absorbing moisture released from the human body; and
wherein said diaper comprises the wireless communication device according to claim 16.

19. A notification system comprising:
the diaper according to claim 18; and
a device which notifies that said diaper is in contact with moisture.

20. A method of producing the circuit according to claim 5, the method comprising the step of forming said semiconductor layer in said transistor by application.

* * * * *